(12) United States Patent
Aubry et al.

(10) Patent No.: US 6,486,360 B1
(45) Date of Patent: Nov. 26, 2002

(54) SINGLET OXYGEN OXIDATION OF ORGANIC SUBSTRATES

(75) Inventors: Jean-Marie Aubry, Oignies (FR); Veronique Rataj-Nardello, Villeneuve d'Ascq (FR); Paul Alsters, Maastricht (NL)

(73) Assignee: DSM Fine Chemicals Austria NFG GmbH & CO KG, Linz (AT)

( * ) Notice: Subject to any disclaimer, the term of this patent is extended or adjusted under 35 U.S.C. 154(b) by 0 days.

(21) Appl. No.: 09/937,725

(22) PCT Filed: Mar. 23, 2000

(86) PCT No.: PCT/EP00/02553

§ 371 (c)(1),
(2), (4) Date: Sep. 28, 2001

(87) PCT Pub. No.: WO00/64842

PCT Pub. Date: Nov. 2, 2000

(30) Foreign Application Priority Data

Apr. 26, 1999 (AT) .................................................. 730/99

(51) Int. Cl.⁷ ........................ C07C 409/00; C07B 41/00
(52) U.S. Cl. .................... 568/569; 568/469.9; 568/558; 568/567; 568/568; 568/577
(58) Field of Search .............................. 568/469.9, 558, 568/567, 568, 569, 577

(56) References Cited

U.S. PATENT DOCUMENTS 4,022,841 A    5/1977  Angstadt

FOREIGN PATENT DOCUMENTS

| EP | 0 288 337 | 10/1988 |
| WO | 97/29066 | 8/1997 |

OTHER PUBLICATIONS

J. M. Aubry, J. Am. Chem. Soc., 1985, vol. 107, pp. 5844–5849.*
Barton et al., J. Chem. Soc., Perkin Transactions I, 1975, pp. 1610–1614.*
Barton et al., Journal of the Chemical Society, Perkin Transactions 1, pp. 1610–1614 (1975).
Griffith, Polyhedron, vol. 15, No. 20, pp. 3493–3500 (1996).

* cited by examiner

*Primary Examiner*—Johann Richter
*Assistant Examiner*—Elvis O. Price
(74) *Attorney, Agent, or Firm*—Wenderoth, Lind & Ponack, L.L.P.

(57) ABSTRACT

The invention relates to a method for oxidizing organic substrate by using $^1O_2$. According to the inventive method, organic substrates that react with $^1O_2$ are mixed with 30–70% $H_2O_2$ in water, in an organic solvent or in a mixture thereof in the presence of a lanthanide as the catalyst. $H_2O_2$ is catalytically decomposed to water and $^1O_2$ and is then oxidized to the corresponding oxidation products.

8 Claims, No Drawings

SINGLET OXYGEN OXIDATION OF ORGANIC SUBSTRATES

This is the National Phase Application of PCT/EP00/02553, filed Mar. 23, 2000.

The only singlet oxygen oxidation ($^1O_2$-Ox) which is currently carried out industrially is the photochemical $^1O_2$-Ox in which the $^1O_2$ is generated by a photochemical route. The disadvantage of this process is given by the high costs of the photochemical equipment required, and by a limited service life. The required lamps degenerate relatively rapidly during the oxidation as a result of soiling of the glass surface. In addition, this process is not suitable for colored substrates. The process is actually suitable only for fine chemicals which are prepared on a relatively small scale. (La Chimica e l'Industria, 1982, Vol. 64, page 156).

For this reason, attempts have been made to find other process variants for the $^1O_2$-Ox which are suitable for the $^1O_2$-Ox of non-water-soluble, hydrophobic organic substrates.

J. Am. Chem. Soc., 1968, 90, 975 describes, for example, the classical "dark" $^1O_2$-Ox in which $^1O_2$ is not generated photochemically, but chemically. In this process, hydrophobic substrates are oxidized by means of a hypochlorite/$H_2O_2$ system in a solvent mixture of water and organic solvent. However, this process has only found a few synthetic applications since many substrates are only sparingly soluble in the required medium. In addition, the use possibility is rather limited because of secondary reactions between hypochlorite and substrate or solvent. In addition, a large part of the $^1O_2$ is deactivated in the gas phase. In addition, this process is not suitable for industrial scale since in the organic medium addition of the hypochlorite on $H_2O_2$ results, and a large excess of $H_2O_2$ is required to suppress the secondary reaction of substrate with hypochlorite. An additional disadvantage arises as a result of the formation of stoichiometric amounts of salt.

A variant of the "dark" $^1O_2$-$O_x$, which is not based on hypochlorite and thus should partly avoid the above disadvantages, is known, for example, from J. Org. Chem., 1989, 54, 726 or J. Mol. Cat., 1997, 117, 439, according to which some water-soluble organic substrates are oxidized with $H_2O_2$ and a molybdate catalyst in water as solvent. According to Membrane Lipid Oxid. Vol. II, 1991, 65, the $^1O_2$-Ox of water-insoluble, organic substrates with the molybdate/$H_2O_2$ system is difficult since it was assumed that none of the customary solvents is suitable for maintaining the disproportionation, catalyzed by molybdate, of $H_2O_2$ into water and $^1O_2$. However, the use of molybdenum catalysts also brings other disadvantages with it. For example, in addition to the $H_2O_2$ disproportionation, they also catalyze other undesired oxidations of some substrates. For example, allyl alcohols cannot be effectively peroxidized with the molybdate/$H_2O_2$ system since this group of substances is epoxidized by molybdenum in the presence of $H_2O_2$. A further disadvantage of these catalysts is the relatively low pH range in which they function. These catalysts can only be used in the basic range between pH9 and pH 12, the use of this system is accordingly unsuitable for acidic conditions.

Accordingly, it was an object of the present invention to catalysts for the $H_2O_2$ disproportionation for "dark" $^1O_2$-Ox which are effective in a broad pH range, in particular including in the acidic range and which do not catalyze undesired secondary reactions, such as, for example, the epoxidation of allylic alcohols, in addition to the $H_2O_2$ disproportionation.

Unexpectedly, it has now been found that lanthanides are effective as catalysts both in the basic and also in the acidic range, with undesired secondary reactions not arising or arising only to a considerably lesser degree when said lanthanides are used. Unexpectedly, these catalysts are also active in heterogeneous form, meaning that their recovery from the reaction mixture can be carried out in a simple way.

Accordingly, the present invention provides a process for the oxidation of organic substrates by means of $^1O_2$, which comprises adding 30–70% strength $H_2O_2$ to organic substrates which react with $^1O_2$ in water, in an organic solvent or in water/solvent mixtures in the presence of a lanthanide as catalyst, whereupon, following the catalytic decomposition of $H_2O_2$ to give water and $^1O_2$, oxidation to give the corresponding oxidation products takes place.

The process according to the invention is suitable for the oxidation of organic substrates which react with $^1O_2$.

Accordingly, substrates which may be used are the following compounds: olefins which contain one or more, i.e. up to 10, preferably up to 6, particularly preferably up to 4 C=C double bonds; electron-rich aromatics, such as $C_6$–$C_{50}$, preferably up to $C_{30}$, particularly preferably up to $C_{20}$, phenols, polyalkylbenzenes, polyalkoxybenzenes; polycyclic aromatics having 2 to 10, preferably up to 6, particularly preferably up to 4 aromatic rings; sulfides, such as, for example, alkyl sulfides, alkenyl sulfides, aryl sulfides which are either mono- or disubstituted on the sulfur atom, and heterocycles having an O, N or S atom in the ring, such as, for example, $C_4$–$C_{50}$, preferably up to $C_{30}$, particularly preferably up to $C_{20}$, furans, $C_4$–$C_{50}$, preferably up to $C_{30}$, particularly preferably up to $C_{20}$, pyrroles, $C_4$–$C_{60}$, preferably up to $C_{30}$, particularly preferably up to $C_{20}$, thiophenes. In this connection, the substrates may have one or more substituents, such as halogen (F, Cl, Br, I), cyanide, carbonyl groups, hydroxyl groups, $C_1$–$C_{50}$, preferably up to $C_{30}$, particularly preferably up to $C_{20}$, alkoxy groups, $C_1$–$C_{50}$, preferably up to $C_{30}$, particularly preferably up to $C_{20}$, alkyl groups, $C_6$–$C_{50}$, preferably up to $C_{30}$, particularly preferably up to $C_{20}$, aryl groups, $C_2$–$C_{50}$, preferably up to $C_{30}$, particularly preferably up to $C_{20}$, alkenyl groups, $C_2$–$C_{50}$, preferably up to $C_{30}$, particularly preferably up to $C_{20}$, alkynyl groups, carboxylic acid groups, ester groups, amide groups, amino groups, nitro groups, silyl groups, silyloxy groups, sulfone groups, sulfoxide groups. In addition, the substrates may be substituted by one or more $NR^1R^2$ radicals in which $R^1$ or $R^2$ may be identical or different and are H; $C_1$–$C_{50}$, preferably up to $C_{30}$, particularly preferably up to $C_{20}$, alkyl; formyl; $C_2$–$C_{50}$, preferably up to $C_{30}$, particularly preferably up to $C_{20}$, acyl; $C_7$–$C_{50}$, preferably up to $C_{30}$, particularly preferably up to $C_{20}$, benzyl, where $R^1$ and $R^2$ may also together form a ring, such as, for example, in a phthalimido group.

Examples of suitable substrates are: 2-butene; isobutene; 2-methyl-1-butene; 2-hexene; 1,3-butadiene; 2,3-dimethylbutene; $\Delta^{9,10}$-octalin, 2-phthalimido-4-methyl-3-pentene; 2,3-dimethyl-1,3-butadiene; 2,4-hexadiene; 3-methyl-2-buten-1-ol; 4-methyl-3-penten-2-ol; 2-amino-4-methyl-3-pentene; 2-chloro-4-methyl-3-pentene; 2-bromo-4-methyl-3-pentene; 1-trimethylsilylcyclohexene; 2,3-dimethyl-2-butenyl-para-tolylsulfone; 2,3-dimethyl-2-butenyl-para-tolyl sulfoxide; N-cyclohexenylmorpholine; 2-methyl-2-norbornene; terpinolene; α-pinene; β-pinene; β-citronellol; ocimene; citronellol; geraniol; farnesol; terpinene; limonene; trans-2,3-dimethyl-acrylic acid; α-terpinene; isoprene; cyclopentadiene; 1,4-diphenylbutadiene; 2-ethoxybutadiene; 1,1'-dicyclohexenyl; cholesterol; ergosterol acetate; 5-chloro-1,3- cyclohexadiene; 3-methyl-2-buten-1-ol; 3,5,5-trimethylcyclohex-2-en-1-ol; phenol, 1,2,4-trimethoxybenzene, 2,3,6-trimethylphenol, 2,4,6-trimethylphenol, 1,4-dimethylnaphthalene, furan, furfuryl alcohol, furfural, 2,5-dimethylfuran, isobenzofuran, dibenzyl sulfide, (2-methyl-5-tert-butyl)phenyl sulfide etc.

As a result of the oxidation according to the invention, the corresponding oxidation product is obtained from the substrates. Alkenes, (polycyclic) aromatics or heteroaromatics give, in particular, hydroperoxides or peroxides which are able to further react under the reaction conditions to give alcohols, epoxides, acetals or carbonyl compounds, such as ketones, aldehydes, carboxylic acids or esters, if the hydroperoxide or the peroxide is unstable.

The oxidation according to the invention is carried out in water or an organic solvent.

Accordingly, suitable solvents are water, $C_1$–$C_8$-alcohols, such as methanol, ethanol, propanol, isopropanol, butanol, isobutanol; ethylene glycol, propylene glycol, formamide, N-methylformamide, dimethylformamide, sulfolane, propylene carbonate.

Preference is given to using methanol, ethanol, propanol, isopropanol, ethylene glycol, propylene glycol, formamide, N-methylformamide or dimethylformamide, particularly preferably methanol, ethanol, ethylene glycol, propylene glycol, formamide or dimethylformamide as solvent.

The reaction can also be carried out in a water/solvent mixture or in a mixture of the above organic solvents.

A metal, namely a lanthanide, is added to the solvent/substrate mixture as heterogeneous or homogeneous inorganic catalyst. Suitable lanthanides are lanthanum, cerium, praseodymium, neodymium, samarium, europium, gadolinium, terbium, dysprosium, holmium, erbium, ytterbium and lutetium, and the so-called pseudo-lanthanides scandium and yttrium. Preference is given to using lanthanum.

In this connection, the metal can be in forms customary for $^1O_2$ oxidations, for example as the oxide, oxo complex, nitrate, carboxylate, hydroxide, carbonate, chloride, fluoride, sulfate, tetrafluoroborate, etc. Where appropriate, a hydroxide, for example NaOH, KOH, etc., can be added to homogeneous, soluble forms of the catalyst to give a heterogeneous, active catalyst.

The amount of catalyst used depends on the substrate used and is between 1 and 15 mol %, preferably between 5 and 25 mol %.

This is followed by the addition of 30–70% strength, preferably 40–60% strength, $H_2O_2$. $H_2O_2$ is preferably added slowly or in portions to the reaction mixture of solvent, substrate and catalyst, the reaction mixture being stirred. It is also possible to firstly add only some of the $H_2O_2$ to a soluble form of the chosen catalyst, then to add a hydroxide, such as, for example, NaOH, KOH etc., and thereafter the residual amounts of $H_2O_2$.

In the process according to the invention, the consumption of $H_2O_2$ is dependent on the substrate used. For reactive substrates, 2 to 3 equivalents of $H_2O_2$ are preferably needed, while less reactive substrates are preferably reacted with 3 to 10 equivalents of $H_2O_2$.

The reaction temperature is between 0 and 50° C., preferably between 15 and 35° C. If the reaction is carried out in water, then the pH of the reaction mixture depends on the substrate chosen. The pH is between 0 and 14, preferably between 4 and 14. The pH of the reaction mixture can be adjusted where necessary as required using customary basic or acidic additives.

The course of the reaction can be monitored by means of UV spectroscopy or by means of HPLC. When the reaction is complete, i.e. after 1 to 30 hours, depending on the reaction conditions, the reaction mixture is worked up and the catalyst is separated off by customary methods.

Particularly in cases where a heterogeneous catalyst is used, separating off the catalyst is very readily possible by simple filtration OR CENTRIFUGATION, as a result of which recycling of the catalyst is also simplified.

The end-product which remains can, where appropriate, be purified by means of recrystallization, extraction or distillation.

The process according to the invention permits the oxidation of a large number of compounds. Accordingly, the process according to the invention is particularly suitable for the oxidation of unsaturated organic compounds, such as allyl alcohols, unsaturated amines, such as allylamines, terpenes, for example α-terpinene and citronellol, aromatic polycycles, steroids, furans, cyclopentadienes, phenols etc., and generally for all compounds which react with $^1O_2$.

The process according to the invention gives the desired end-products in high yields of up to 100% with high purity.

The process according to the invention is characterized by the simple process regime which is best suited to the industrial scale since it can take place in simple multipurpose plants and with simple work-up steps, and can be used for a wide spectrum of substrates.

EXAMPLE 1

Oxidation of α-terpinene

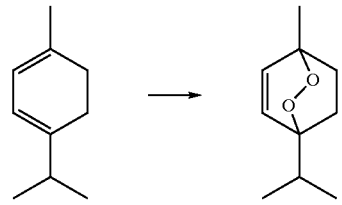

At 30° C., 230 μl of $H_2O_2$ (50%) and 200 μl of 5M NaOH were successively added to a solution of 325 μl of α-terpinene and 143.6 mg of $La(NO_3)_3 \cdot xH_2O$ in 4 ml of methanol, whereupon a white precipitate formed. After 3.5 hours and after 21 hours, two further 230 μl portions of $H_2O_2$ (50%) were added to the mixture. After 24.5 hours, the reaction mixture was centrifuged, and the solution was decanted from the catalyst. The solvent was evaporated and the residue was dissolved in $CDCl_3$ and analyzed using NMR. The reaction mixture was also analyzed by means of HPLC (MeOH/$H_2O$ 90/10; 260 nm). The analyses gave a conversion of 10% and a yield of >90% of ascaridol.

EXAMPLE 2

Oxidation of β-citronellol

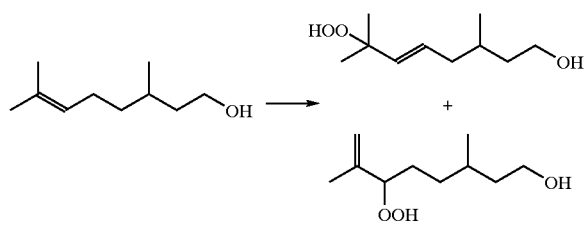

At 25° C., 300 μl of $H_2O_2$ (50%) and 200 μl of 5M NaOH were successively added to a solution of 391 mg of β-citronellol and 163 mg of La(NO$_3$)$_3$.xH$_2$O in 5 ml of methanol, whereupon a white precipitate formed. After 1.3 hours and after 4.0 hours, two further 300 µl portions of H$_2$O$_2$ (50%) were added to the mixture. After 5.75 hours, the reaction mixtures [sic] was analyzed by means of HPLC (MeOH/H$_2$O 70/30 v/v; 200 nm). The analysis gave a conversion of 61% with a yield of secondary hydroperoxide of 24% and a yield of tertiary hydroperoxide of 37%.

EXAMPLE 3

Oxidation of sodium 2-methyl-2-butenoate

At 25° C., 150 µl of H$_2$O$_2$ (50%) were added to a solution of 50 mg of sodium 2-methyl-2-butenoate and 138 mg of La(NO$_3$)$_3$.xH$_2$O in 4 ml of D$_2$O, whereupon a white precipitate formed. After 0.75 hours and after 2.0 hours, two further 150 µl portions of H$_2$O$_2$ (50%) were added to the mixture. After 3.3 hours, the reaction mixture was analyzed by means of NMR. The analysis gave a conversion of 48% with a hydroperoxide yield of 48%.

EXAMPLE 4

Oxidation of 3-methyl-2-butene-1-ol

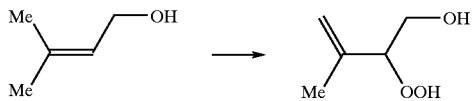

At 25° C., 300 µl of H$_2$O$_2$ (50%) and 200 µl of 5M NaOH were successively added to a solution of 215 mg of 3-methyl-2-buten-1-ol and 163 mg of La(NO$_3$)$_3$.xH$_2$O in 5 ml of methanol, whereupon a white precipitate formed. After 1.0 hour and after 4.3 hours, two further 300 µl portions of H$_2$O$_2$ (50%) were added to the mixture. After 6.0 hours, the reaction mixture was centrifuged and the solution was decanted from the catalyst. The solvent was evaporated, and the residue was dissolved in CDCl$_3$ and analyzed with NMR. The analysis gave a conversion of 100% with a hydroperoxide yield of 70%.

EXAMPLE 5

Oxidation of mesitylol

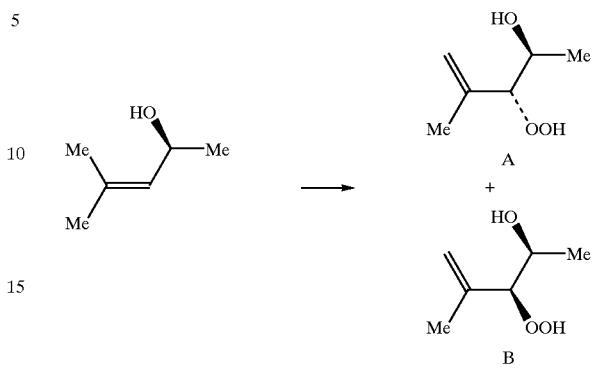

At 25° C., 300 µl of H$_2$O$_2$ (50%) and 200 µl of 5M NaOH were successively added to a solution of 257 mg of mesitylol and 163 mg of La(NO$_3$)$_3$. xH$_2$O in 5 ml of methanol, whereupon a white precipitate formed. After 1.0 hour and after 4.3 hours, two further 300 µl portions of H$_2$O$_2$ (50%) were added to the mixture. After 6.0 hours, the reaction mixture was centrifuged and the solution was decanted from the catalyst. The solvent was evaporated, and the residue was dissolved in CDCl$_3$ and analyzed with NMR. The analysis gave a conversion of 100% with a yield of hydroperoxide A of 62% and a yield of hydroperoxide B of 38%.

Comparative Experiment

Oxidation of 3-methyl-2-buten-1-ol with sodium molybdate as catalyst

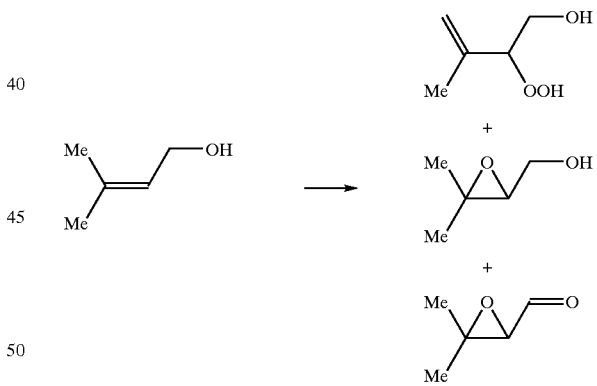

At 25° C., 100 µl of H$_2$O$_2$ (50%) were added to a suspension of 100 ml of 3-methyl-2-buten-1 -ol and 121 mg of Na$_2$MoO$_4$.4H$_2$O in 5 ml of methanol, whereupon a clear orange-red solution formed. After 21 minutes, 42 minutes, 60 minutes, 86 minutes, 120 minutes, 144 minutes, 206 minutes, 224 minutes, 270 minutes, 300 minutes and 333 minutes, 11 further 100 µl portions of H$_2$O$_2$ (50%) were added to the mixture. After 6.5 hours, the reaction mixture was centrifuged and the solution was decanted from the catalyst. The solvent was evaporated and the residue was dissolved in CDCl$_3$ and analyzed with NMR. The analysis gave a conversion of 100% with a yield of hydroperoxide of 31%, of epoxy alcohol of 59%, and of epoxy aldehyde of 10%.

Comparative Experiment

Photo-oxygenation of mesitylol

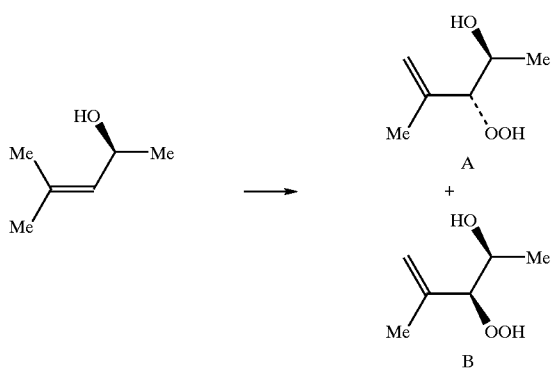

At −10° C., oxygen was passed through a solution of 40 mg of mesitylol and a trace of methylene blue in 4 ml of $CD_3OD$, with irradiation with an Na lamp. After 3.0 hours, the solution was analyzed with NMR. The analysis gave a conversion of 100% with a yield of hydroperoxide A of 65% and a yield of hydroperoxide B of 35%.

What is claimed is:

1. A process for the oxidation of organic substrates by means of $^1O_2$, which comprises adding 30–70% strength $H_2O_2$ to organic substrates which react with $^1O_2$ in water, an organic solvent or a water/solvent mixture in the presence of a lanthanide or pseudo-lanthanide as catalyst, wherein the lanthanides used are lanthanum, praseodymium, neodymium, samarium, europium, gadolinium, terbium, dysprosium, holmium, erbium, ytterbium or lutetium, or the pseudo-lanthanides used are scandium or yttrium, wherein the catalysts based on lanthanides or pseudo-lanthanides are in the form of oxo complexes, nitrates, carboxylates, hydroxides, carbonates, chlorides, fluorides, sulfates or tetrafluoroborates, at a reaction temperature of 0 to 50° C. whereupon, following the catalytic decomposition of $H_2O_2$ to give water and $^1O_2$, oxidation to give the corresponding oxidation products takes place.

2. The process as claimed in claim 1, wherein the substrates which react with $^1O_2$ used are olefins which contain 1 to 10 C=C double bonds; $C_6$–$C_{50}$ phenols, polyalkylbenzenes, polyalkoxybenzenes; polycyclic aromatics having 2 to 10 aromatic rings; alkyl sulfides, alkenyl sulfides, aryl sulfides which are either mono- or disubstituted on the sulfur atom, and $C_4$–$C_{60}$ heterocycles having an O, N or S atom in the ring, which may be unsubstituted or may be mono- or polysubstituted by halogens, cyanide, carbonyl groups, hydroxyl groups, $C_1$–$C_{50}$ alkoxy groups, $C_1$–$C_{50}$ alkyl groups, $C_6$–$C_{50}$ aryl groups, $C_2$–$C_{50}$ alkenyl groups, $C_2$–$C_{50}$ alkynyl groups, carboxylic acid groups, ester groups, amide groups, amino groups, nitro groups, silyl groups, silyloxy groups, sulfone groups, sulfoxide groups or by one or more $NR^1R^2$ radicals in which $R^1$ or $R^2$ may be identical or different and are H; $C_1$–$C_{50}$alkyl; formyl; $C_2$–$C_{50}$ acyl; $C_7$–$C_{50}$ benzyl, where $R^1$ and $R^2$ may also together form a ring.

3. The process as claimed in claim 1, wherein the solvent used is water, $C_1$–$C_8$-alcohols, ethylene glycol, propylene glycol, formamide, N-methylformamide, dimethylformamide, sulfolane, propylene carbonate or mixtures thereof.

4. The process as claimed in claim 1, wherein the solvent used is methanol, ethanol, propanol, isopropanol, ethylene glycol, propylene glycol, formamide, N-methylformamide or dimethylformamide.

5. The process as claimed in claim 1, wherein homogeneous, soluble forms of the catalyst are converted into a heterogeneous, active form of the catalyst by adding a hydroxide.

6. The process as claimed in claim 1, wherein 2 to 10 equivalents of $H_2O_2$ are used depending on the substrate used.

7. The process as claimed in claim 1, wherein the reaction temperature is between 15 and 35° C.

8. The process as claimed in claim 1, wherein a pH between 0 and 14 is set depending on the solvent, substrate and catalyst used.

* * * * *